United States Patent
Ishizu et al.

(10) Patent No.: US 9,676,005 B2
(45) Date of Patent: Jun. 13, 2017

(54) OPTICAL TYPE GRANULE SORTING MACHINE

(71) Applicant: SATAKE CORPORATION, Chiyoda-ku, Tokyo (JP)

(72) Inventors: Hideaki Ishizu, Hiroshima (JP); Tomoyuki Miyamoto, Hiroshima (JP); Masazumi Hara, Hiroshima (JP)

(73) Assignee: Satake Corporation (JP)

( * ) Notice: Subject to any disclaimer, the term of this patent is extended or adjusted under 35 U.S.C. 154(b) by 0 days.

(21) Appl. No.: 14/767,914

(22) PCT Filed: Feb. 17, 2014

(86) PCT No.: PCT/JP2014/053593
§ 371 (c)(1),
(2) Date: Aug. 14, 2015

(87) PCT Pub. No.: WO2014/126232
PCT Pub. Date: Aug. 21, 2014

(65) Prior Publication Data
US 2015/0375270 A1 Dec. 31, 2015

(30) Foreign Application Priority Data
Feb. 18, 2013 (JP) .................. 2013-029082

(51) Int. Cl.
*B07C 5/34* (2006.01)
*B07C 5/342* (2006.01)
(Continued)

(52) U.S. Cl.
CPC ......... *B07C 5/3425* (2013.01); *G01N 21/251* (2013.01); *G01N 21/85* (2013.01);
(Continued)

(58) Field of Classification Search
CPC .................. B07C 5/3425; B07C 5/366; B07C 2501/0018; G01N 21/85; G01N 21/8592; G01J 3/465; G01J 3/467; G01J 2003/467
See application file for complete search history.

(56) References Cited

U.S. PATENT DOCUMENTS

| 3,782,544 | A | * | 1/1974 | Perkins, III | ............... | A24B 1/04 209/565 |
| 5,392,364 | A | * | 2/1995 | Yokoyama | ............... | G06K 9/64 382/190 |

(Continued)

FOREIGN PATENT DOCUMENTS

| JP | H4-61558 A | 2/1992 |
| JP | 2004-178050 A | 6/2004 |

(Continued)

OTHER PUBLICATIONS

International Search Report for PCT/JP2014/053593 dated Apr. 28, 2014.

(Continued)

*Primary Examiner* — Joseph C Rodriguez
(74) *Attorney, Agent, or Firm* — Lerner, David, Littenberg, Krumholz & Mentlik, LLP

(57) ABSTRACT

An optical type granule sorting machine has a determination unit that includes a three-dimensional color distribution data creation section that creates data on wavelength components of R light, G light, and B light from granules in a three-dimensional color space, a Mahalanobis distance interface creation section that partitions the data into a conforming granule cluster area and a nonconforming granule cluster area, a Euclidean distance interface creation section that determines a position of center of gravity of the conforming granule cluster area and a position of center of gravity of the nonconforming granule cluster area to set an interface that allows the positions of center of gravity to lie at a longest (Continued)

distance from each other, a two-dimensional data conversion section that converts into two-dimensional color distribution data by using a line of intersection between the interfaces, and a threshold setting section.

3 Claims, 14 Drawing Sheets

(51) Int. Cl.
    *G01N 21/85*     (2006.01)
    *G01N 21/25*     (2006.01)

(52) U.S. Cl.
    CPC ............... *B07C 2501/0018* (2013.01); *G01N 2021/8592* (2013.01)

(56) References Cited

U.S. PATENT DOCUMENTS

| | | | | |
|---|---|---|---|---|
| 5,487,472 A | * | 1/1996 | Satake | B07C 5/3416 |
| | | | | 209/581 |
| 5,522,491 A | * | 6/1996 | Baudat | G06K 9/52 |
| | | | | 194/207 |
| 5,779,058 A | * | 7/1998 | Satake | B07C 5/3425 |
| | | | | 209/581 |
| 5,931,277 A | * | 8/1999 | Allan | G06K 9/6215 |
| | | | | 194/317 |
| 7,968,814 B2 | * | 6/2011 | Imai | B07C 5/3425 |
| | | | | 209/576 |
| 9,024,223 B2 | * | 5/2015 | Miyamoto | B07C 5/342 |
| | | | | 209/580 |
| 2004/0131251 A1 | | 7/2004 | Sasaki | |
| 2005/0067332 A1 | | 3/2005 | Ikeda et al. | |
| 2011/0286659 A1 | | 11/2011 | Saeki | |
| 2015/0076042 A1 | | 3/2015 | Miyamoto et al. | |

FOREIGN PATENT DOCUMENTS

| | | |
|---|---|---|
| JP | 2005-74412 A | 3/2005 |
| JP | 2005-230703 A | 9/2005 |
| JP | 2007-6142 A | 1/2007 |
| JP | 2009-119410 A | 6/2009 |
| JP | 2011-7553 A | 1/2011 |
| WO | WO-2013/145873 A1 | 10/2015 |

OTHER PUBLICATIONS

Written Opinion for PCT/JP2014/053593 dated Apr. 28, 2014.
International Preliminary Report for PCT/JP2014/053593 dated Aug. 18, 2015.

* cited by examiner

OPTICAL TYPE GRANULE SORTING MACHINE

TECHNICAL FIELD

The present invention relates to an optical type granule sorting machine which sorts granules such as grains such as rice or wheat or resin pellets into conforming granules and nonconforming granules and which removes foreign substances mixed in the granules by blowing air against the granules.

BACKGROUND ART

Conventionally, in an optical type granule sorting machine, before sorting operation, an operator changes a reference threshold set in advance in optical detection means to adjust a sensitivity level. The adjustment of the sensitivity level allows adjustment of the type of foreign substances (glass pieces, stones, and the like) to be sorted and removed from sorting targets or adjustment of the type of colored granules (nonconforming granules, milky rice, slightly altered rice, and the like) to be sorted and removed from sorting targets. Setting the sensitivity level at a proper value as described above allows precise removal of foreign substances, colored granules, and other nonconforming granules. That is, too low sensitivity causes imprecise determination of whether sorting granules are conforming or nonconforming granules and therefore causes unintended operation of exclusion means, resulting in nonconforming granules being mixed in with conforming granules. On the other hand, too high sensitivity causes excessive exclusion operation of the exclusion means and hence causes conforming granules to be sorted as well as nonconforming granules, resulting in a decrease in yield.

The adjustment of the sensitivity level before the sorting operation is cumbersome for an operator, or frequent adjustment of the sensitivity level could cause instability in sorting accuracy. To solve the problem described above, there has been proposed a color sorting machine that displays an image of a granule captured with a CCD sensor or any other image pickup means and allows an operator who looks at the displayed image to perform the sensitivity adjustment (see Patent Literature 1).

The color sorting machine includes transfer means for continuously transferring granules and illumination means for illuminating the granules being transferred in a detection position. The color sorting machine further includes image pickup means for picking up an image of the illuminated granules in the detection position and exterior shape processing means for outputting the contour shape of a granule in the form of exterior shape binary data based on comparison between an image signal from the image pickup means and an exterior shape threshold. The color sorting machine still further includes no-conformation determination means for determining a granule having a portion having a density greater than a threshold corresponding to a predetermined density to be a nonconforming granule and outputting the nonconforming portion of the nonconforming granule in the form of nonconforming pixel binary data. The color sorting machine still further includes granule display means for combining the exterior shape binary data from the exterior shape processing means with the nonconforming pixel binary data from the no-conformation determination means and displaying the combined data and nonconforming granule display means for displaying the nonconforming pixel binary data from the no-conformation determination means.

The color sorting machine still further includes a display adjustment mechanism including threshold adjustment means for allowing an operator who looks at the display means to change the threshold.

The thus configured color sorting machine, which allows the operator to adjust the sensitivity after checking a nonconforming granule having been determined to be nonconforming based on set sensitivity by using the display means, is advantageously effective in that the sensitivity can be adjusted more accurately.

The color sorting machine described in Patent Literature 1 displays an image of a granule on the operation panel and allows the operator who looks at the displayed image to adjust the sensitivity. In this process, the operator could be undesirably required, for example, to make decision on or possess knowhow about, for example, the type and degree of foreign substances to be sorted and removed or the type and degree of colored granules to be sorted and removed.

CITATION LIST

Patent Literature

Patent Literature 1 Japanese Patent Laid-Open No. 2005-74412

SUMMARY OF INVENTION

Technical Problem

With the foregoing in view, it is a technical object of the present invention to provide an optical type granule sorting machine which allows a threshold setting to be performed by effectively utilizing RGB three-dimensional color space information similar to information obtained via human eyes and which eliminates a need for an operator's decision, knowhow, or other abilities in sensitivity adjustment.

Solution to Problem

To accomplish the object, the present invention takes technical measures by providing an optical type granule sorting machine comprising transfer means for transferring granules including conforming granules, nonconforming granules, and foreign substances in such a manner that the granules form a continuous flow, inspection means for inspecting the granules transferred by the transfer means, determination means for determining whether or not the granules are to be treated as a separation target based on information on color of the individual granules inspected by the inspection means, and exclusion means for excluding the separation target determined by the determination means from the continuous flow, wherein the inspection means includes an illumination section that illuminates the granules with light and an optical detection section that detects light transmitted through the granules or reflected from the granules, and the determination means includes a three-dimensional color distribution data creation section that plots wavelength components of R light, G light, and B light from the granules detected by the optical detection section in a three-dimensional color space to create three-dimensional color distribution data for a granule sample, a Mahalanobis distance interface creation section that sets an interface calculated based on a Mahalanobis distance in the three-dimensional color distribution data created by the three-dimensional color distribution data creation section to partition the data into a first conforming granule cluster area containing many conforming granules and a first nonconforming granule cluster area containing many nonconforming granules and foreign substances, a Euclidean distance interface creation section that determines a position of center of gravity of the first conforming granule cluster area created by the Mahalanobis distance interface creation section and a position of center of gravity of the first nonconforming granule cluster area created by the Mahalanobis distance interface creation section, the Euclidean distance interface creation section setting an interface calculated based on a Euclidean distance at which the positions of center of gravity lie at a longest distance from each other to partition the data into a second conforming granule cluster area and a second nonconforming granule cluster area, a two-dimensional data conversion section that determines a line of intersection between the interface calculated based on the Mahalanobis distance and the interface calculated based on the Euclidean distance and converts the three-dimensional color distribution data into two-dimensional color distribution data in such a way that a viewpoint is placed on the line of intersection, and a threshold setting section that creates a closed area by fitting an inertia equivalent ellipse to the nonconforming granule cluster area on the two-dimensional color distribution data converted by the two-dimensional data conversion section and sets a threshold in the closed area.

Advantageous Effects of Invention

Thus, an optical type granule sorting machine can be provided which allows a threshold setting to be performed by effectively utilizing RGB three-dimensional color space information similar to information obtained via human eyes and which eliminates a need for an operator's decision, knowhow, or other abilities in sensitivity adjustment.

DETAILED DESCRIPTION

Figure 1:
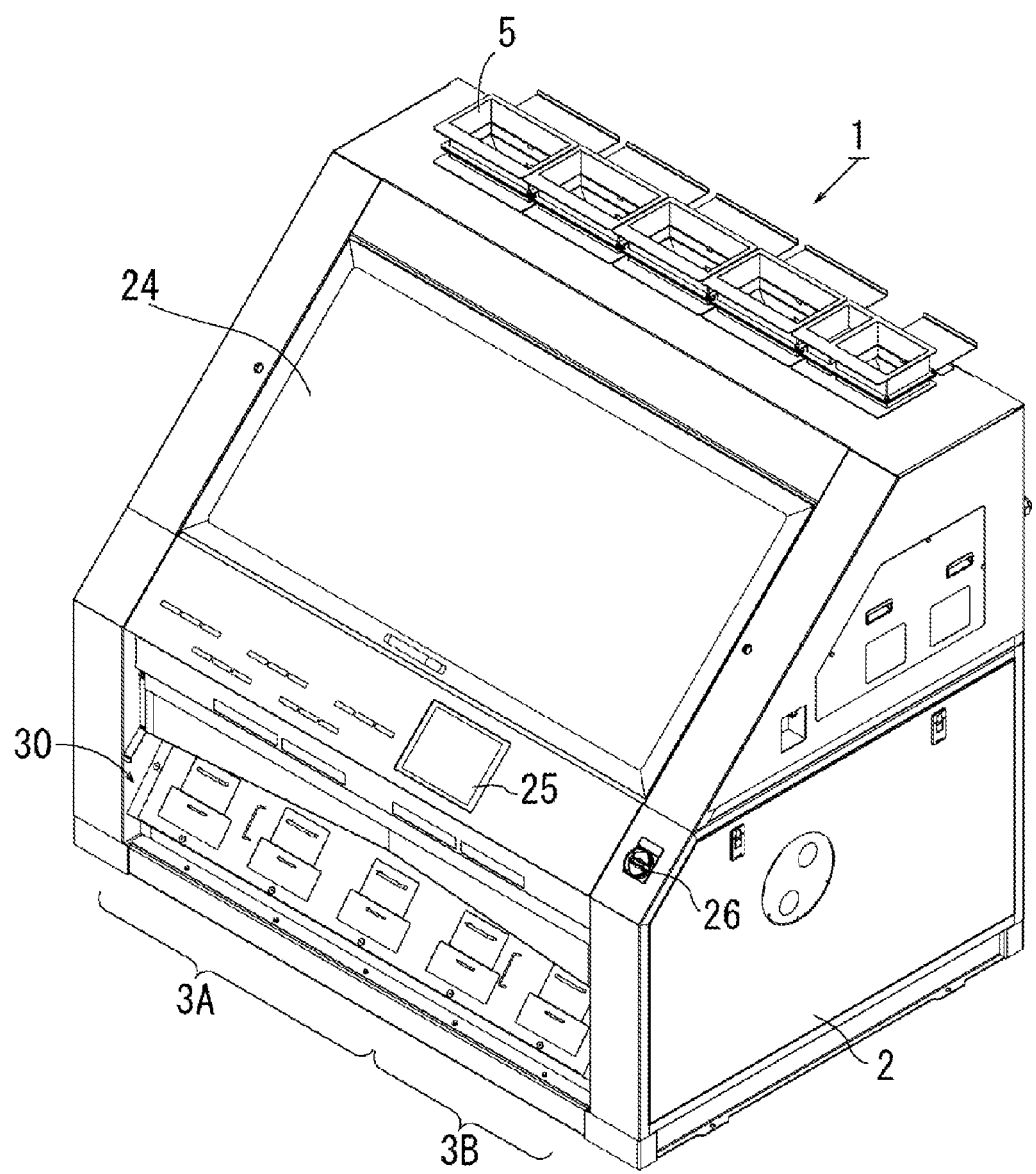
FIG. 1 is a perspective view depicting a whole optical type granule sorting machine in an embodiment.
Figure 2:
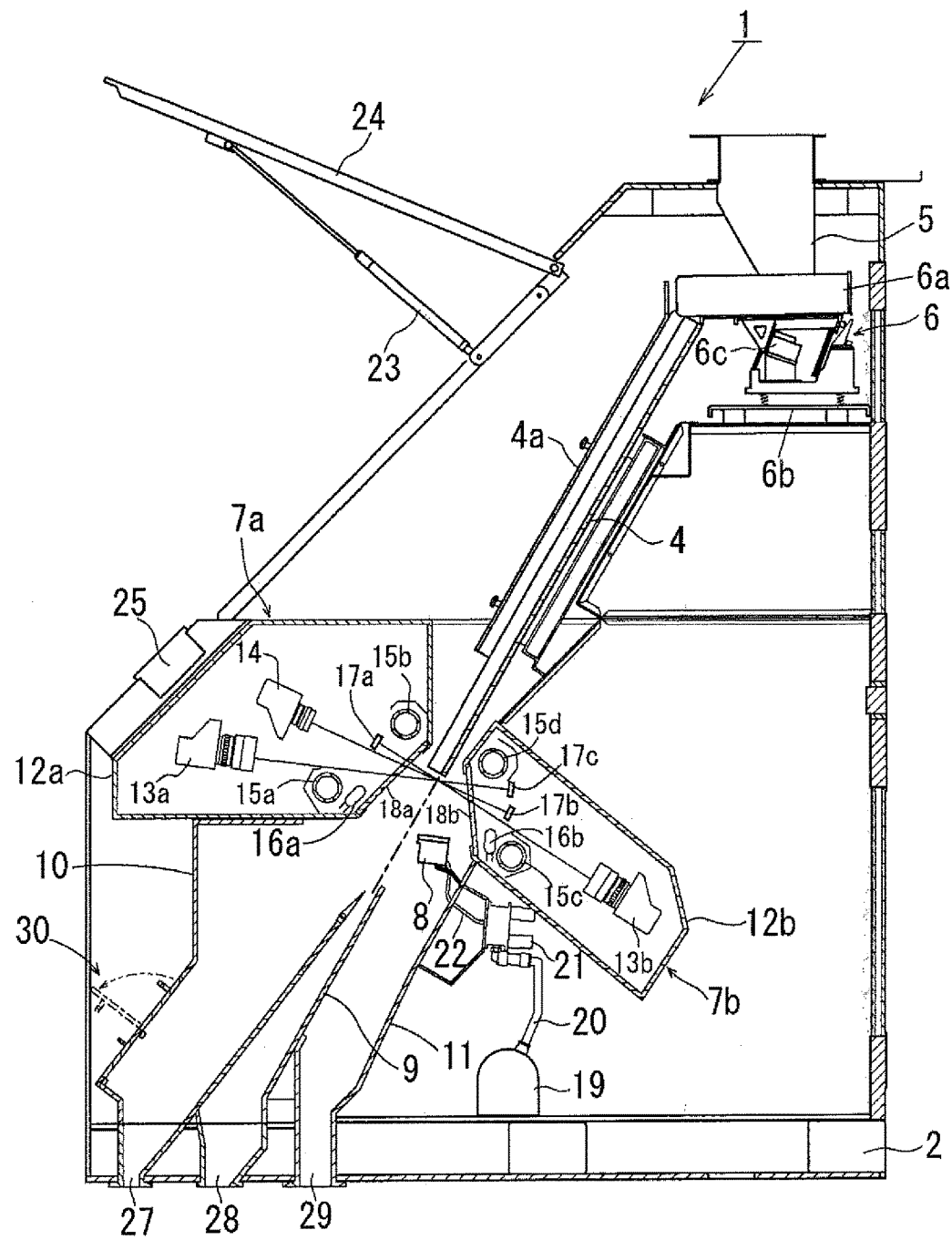
FIG. 2 is a schematic vertical cross-sectional view depicting the internal structure of the sorting machine.
Figure 3:
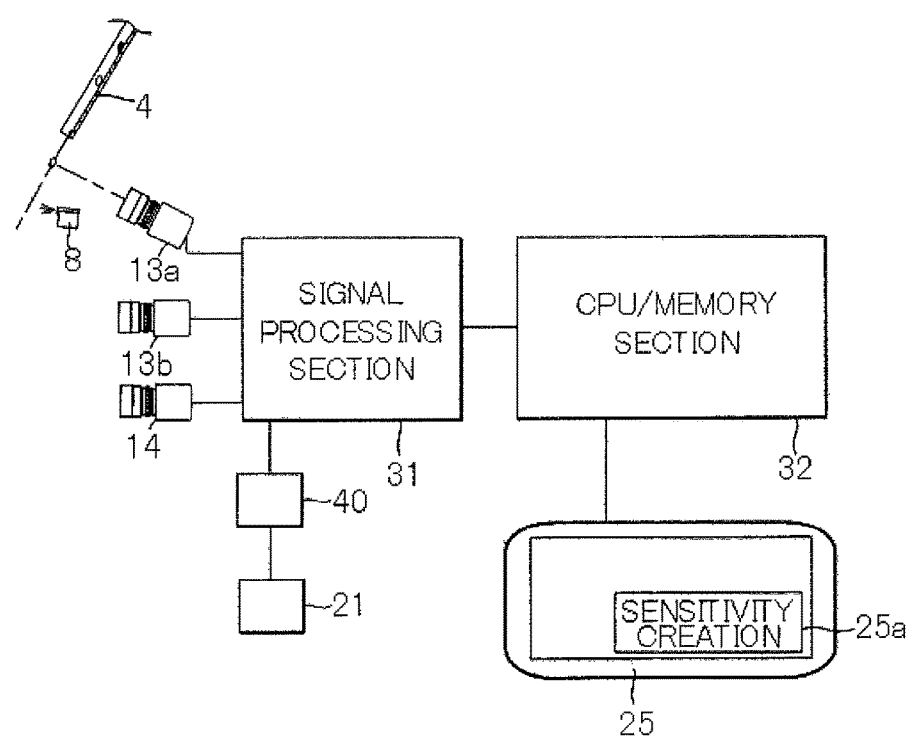
FIG. 3 is a block diagram of signal processing means for processing signals obtained from a camera in the sorting machine.
Figure 4:
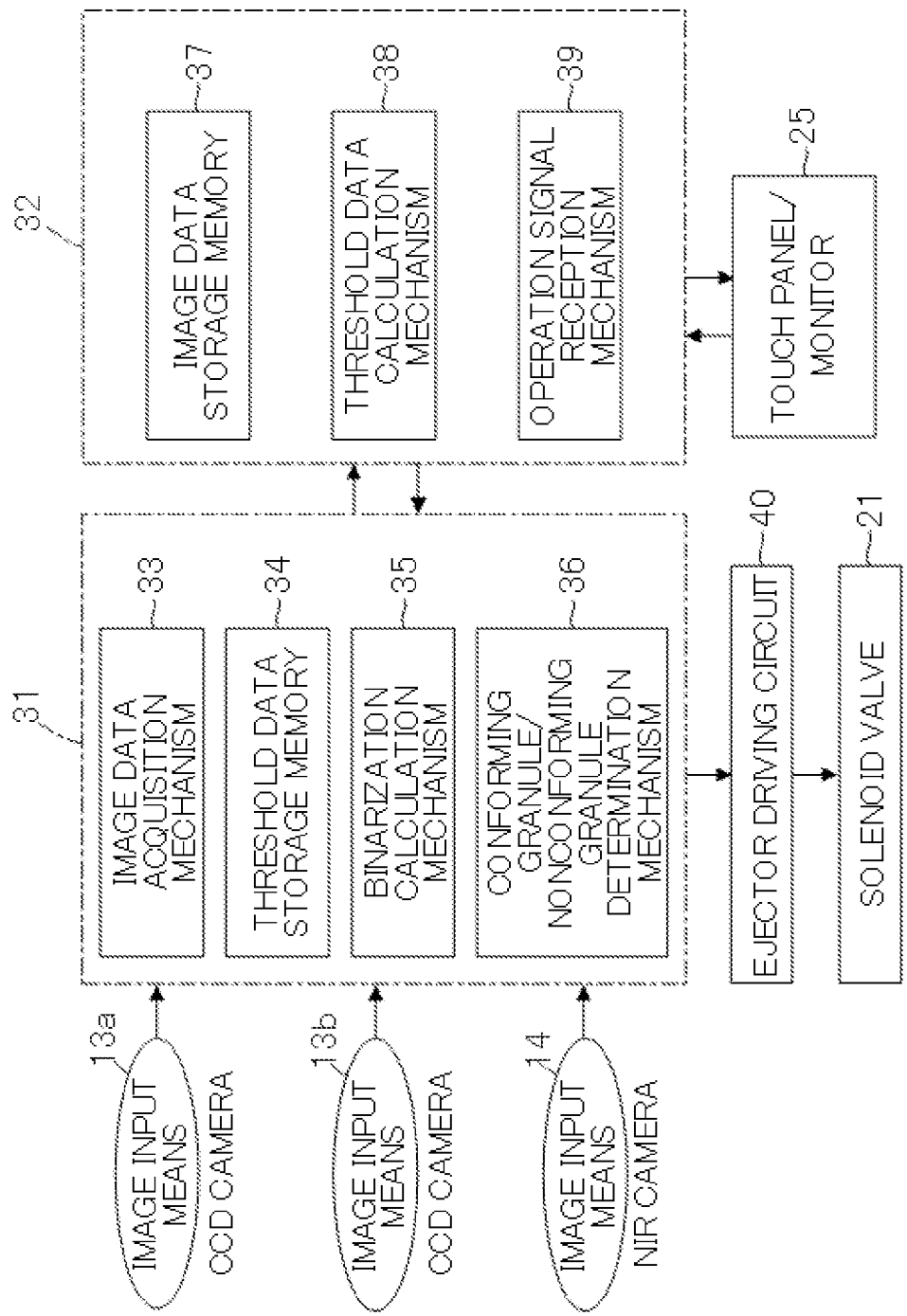
FIG. 4 is a block diagram conceptually illustrating a signal processing section and a CPU and a memory all depicted in FIG. 3.

An embodiment of the present invention will be described with reference to the drawings. FIG. 1 is a perspective view depicting the whole optical type granule sorting machine according to the present embodiment. FIG. 2 is a schematic vertical cross-sectional view depicting the internal structure of the sorting machine. FIG. 3 is a block diagram of signal processing means for processing signals obtained from a camera in the sorting machine. FIG. 4 is a conceptual diagram illustrating the internal structure of a signal processing section and a CPU and a memory all depicted in FIG. 3.

As depicted in FIG. 1, an optical type granule sorting machine 1 includes a generally trapezoidal machine frame 2 in which a plurality of primary sorting sections 3A (up to the third sorting section from the left end of FIG. 1) and a plurality of secondary sorting sections 3B (up to the second sorting section from the right end of FIG. 1) are arranged in juxtaposition. Each of the sorting sections 3A and 3B includes components arranged therein which are similar to corresponding components according to the conventional technique. In the present embodiment, the plurality of primary sorting sections 3A and the plurality of secondary sorting sections 3B are arranged in juxtaposition. However, the present invention is not limited to this, and many variations may be set, such as a configuration in which a plurality of primary sorting sections, a single secondary sorting section, and a single tertiary sorting section are arranged in juxtaposition.

Now, components of the primary sorting section 3A will be described with reference to FIG. 2. The primary sorting section 3A includes a chute 4 serving as transfer means, a storage tank 5 in which granules such as grains are stored, a vibrating feeder 6 that conveys the granules from the storage tank 5 to the chute 4, optical detection sections 7 that detects the granules falling from a lower end of the chute 4, an ejector nozzle 8 provided below the optical detection sections 7, a conforming granule collection gutter 9 provided below the ejector nozzle 8, a nonconforming granule collection gutter 10 juxtaposed with the conforming granule collection gutter 9, and an auxiliary nonconforming granule collection gutter 11. The chute 4 is arranged so as to incline at an angle of about 60 degrees to a horizontal position. The optical detection sections 7 are provided above and below, respectively, a falling trajectory of the granules falling from the lower end of the chute 4. The conforming granule collection gutter 9 receives the granules falling along the falling trajectory without receiving air blown through the ejector nozzle 8. The nonconforming granule collection gutter 10 collects nonconforming granules having received air blown through the ejector nozzle 8. The auxiliary nonconforming granule collection gutter 11 collects nonconforming granules impinging against and bouncing back from peripheral members after failing to receive the air blown through the ejector nozzle 8.

In the primary sorting section 3A, the chute 4 is shaped like a flat plate with no groove portion so as to allow granules to slide over a wide zone. A chute cover 4a is provided at a predetermined distance from a bottom surface of the chute 4 in order to prevent granules from overflowing from the chute 4 and to prevent sorting target granules from floating from the bottom surface during sliding in the chute 4. The chute 4 may instead have a shape different from the shape like a flat plate. The chute cover 4a may be omitted.

The vibrating feeder 6 includes a feeder trough 6a supported on a support section 6b and is configured to be able to feed granules to the chute 4 when a vibration member such as a solenoid coil 6c is actuated.

The optical detection sections 7a and 7b are formed by being enclosed by boxes 12a and 12b, respectively. The box 12a located in front of the falling trajectory of the grains contains a CCD camera 13a for visible light, an NIR camera 14 for near infrared light, visible light sources 15a and 15b each including a fluorescent lamp or any other light source, a near infrared light source 16a including a halogen lamp or any other light source, and a background 17a opposite to the optical detection section 7b. The box 12b located behind the falling trajectory of the grains contains a CCD camera 13b for visible light, visible light sources 15c and 15d each including a fluorescent lamp or any other light source, a near infrared light source 16b including a halogen lamp or any other light source, and backgrounds 17b and 17c opposite to the optical detection section 7a. The boxes 12a and 12b include window members 18a and 18b, respectively, fitted therein on the falling trajectory side of the grains and including transparent glass.

The ejector nozzle 8 is fed with air from an air compressor not depicted in the drawings, through a tube 22 via a subtank 19, an air pipe 20, and a solenoid valve 21. The subtank 19 temporarily stores air from the air compressor. The provision of the subtank 19 prevents shortage of air even if a large amount of air is consumed through the ejector nozzle 8.

An inclined wall in a front portion of the machine frame 2 is provided with a front door 24 that can be rotationally moved in an up-down direction by an air cylinder 23. This enables maintenance work such as cleaning to be facilitated. Below the front door 24, a control panel including a touch panel, a liquid crystal display 25 also serving as a monitor, and a power supply switch 26 are provided. When the liquid crystal display 25 and the power supply switch 26 are disposed at the height position of an operator's eyes, machine operations can be easily performed.

Now, a configuration of the secondary sorting section 3B will be described. A difference between the secondary sorting section 3B and the primary sorting section 3A is the shape of the chute 4; the chute 4 for the secondary sorting section 3B includes a plurality of groove portions formed therein to allow grains to slide so as to be divided into a plurality of columns. An appropriate cross-sectional shape may be adopted for the groove portion; the cross section may be, for example, U- or V-shaped or recessed (none of the shapes is depicted). The remaining part of configuration of the secondary sorting section 3B is approximately similar to the corresponding part of configuration of the primary sorting section 3A. Reference numeral 27 in FIG. 2 denotes a nonconforming granule faucet. Reference numeral 28 in FIG. 2 denotes a conforming granule faucet. Reference numeral 29 denotes an auxiliary nonconforming granule faucet. Reference numeral 30 denotes a sample slot.

A configuration of signal processing means will be described with reference to FIGS. 3 and 4. The CCD cameras 13a and 13b for visible light and the NIR camera 14 are electrically connected to a signal processing section 31 in order to allow a binarization process to be executed on images taken by the cameras. The signal processing section 31 is electrically connected to a CPU and memory section 32 that stores the binarized images from the signal processing section 31 and applies a needed process to the images. The liquid crystal display 25 is electrically connected to the CPU and memory section 32.

Referring to FIG. 4, the signal processing section 31 includes an image data acquisition mechanism 33 that temporarily stores image data, a threshold data storage memory 34, a binarization calculation mechanism 35 that executes a binarization process on the acquired image data, and a conforming granule/nonconforming granule determination mechanism 36 that determines whether the acquired image data indicates conforming granules or nonconforming granules. The threshold data storage memory 34 stores threshold data allowing determination of whether image data acquired by the image data acquisition mechanism 33 indicates conforming granules or nonconforming granules. The CPU and memory section 32 includes an image data storage memory 37 that stores the data from the image data acquisition mechanism 33, a threshold data calculation mechanism 38 that calculates the threshold, and an operation signal reception mechanism 39. The threshold data calculation mechanism 38 calculates the threshold based on the image data stored in the image data storage memory 37. The operation signal reception mechanism 39 receives a signal for a touch operation on the liquid crystal display 25 and outputs the processed image data to the monitor.

An ejector driving circuit 40 is electrically connected to the conforming granule/nonconforming granule determination mechanism 36 in the signal processing section 31. The solenoid valve 21 is electrically connected to the ejector driving circuit 40. The solenoid valve 21 allows air to be blown through the ejector nozzle 8 based on a signal from the ejector driving circuit 40.

The effects of the optical type granule sorting machine configured as described above will be described in detail.

Figure 5:
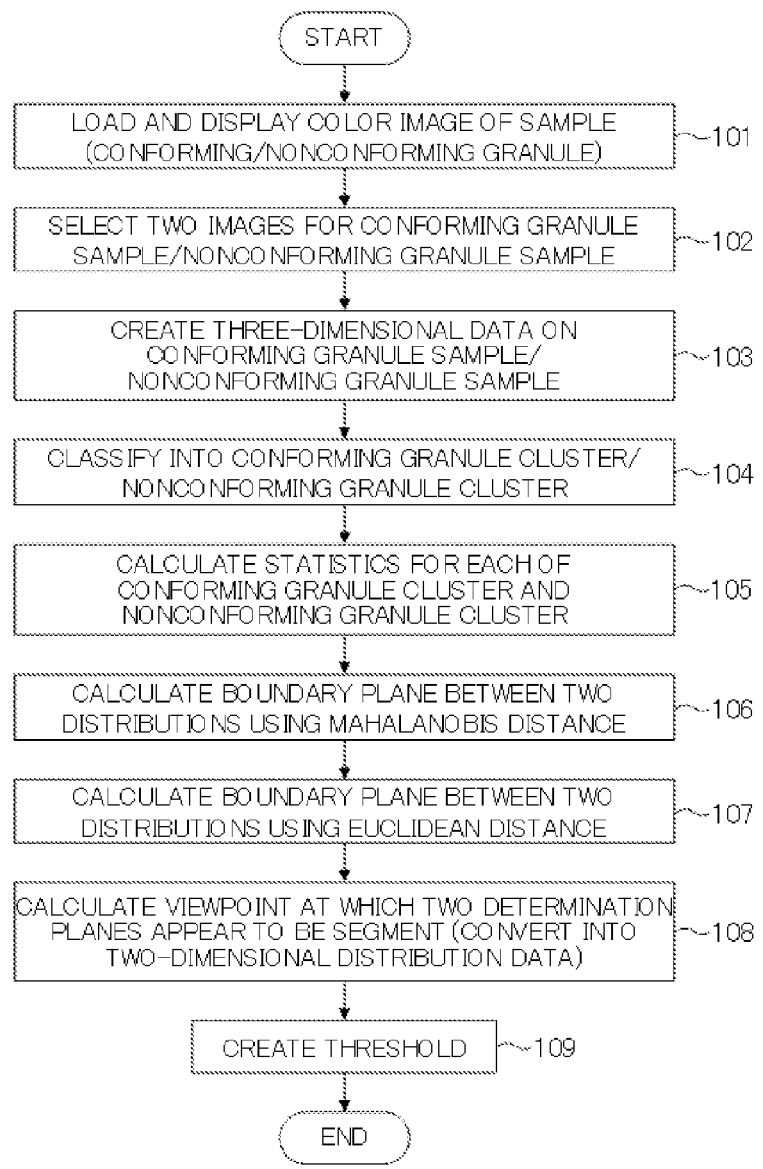
FIG. 5 is a flow diagram depicting an operating procedure executed by the signal processing section.

FIG. 5 is a flowchart depicting an operating procedure for the signal processing section. In FIG. 5, steps 101 to 103 correspond to conforming granule pattern/nonconforming granule pattern learning steps. Steps 104 to 108 correspond to threshold calculation steps of automatically calculating a threshold serving as a boundary between the conforming granule pattern and the nonconforming granule pattern. Step 109 is a threshold determination step in which the threshold calculated in the threshold calculation steps is automatically tuned. In the conforming granule pattern/nonconforming granule pattern learning steps, after samples for a conforming granule, a nonconforming granule, and a foreign substance preliminarily prepared by an operator are allowed to flow through the chute, the sorting machine is allowed to learn three-dimensional color distribution patterns for the conforming granule, the nonconforming granule, and the foreign substance. The threshold determination step is an important part of the present invention.

(Conforming Granule Pattern/Nonconforming Granule Pattern Learning Steps)

The pattern learning steps are a preparatory operation before sorting, and thus, the ejector nozzle 8 is not actuated. When the pattern learning steps are started, in step 101, the conforming granule sample is allowed to flow from the storage tank 5 onto the chute 4. Images of the conforming granule sample falling from a lower end of the chute 4 are picked up by the CCD cameras 13a and 13b and the NIR camera 14. Then, data formed of a large number of images of the conforming granule sample taken by the cameras 13a, 13b, and 14 are input to the image data storage memory 37 via the image data acquisition mechanism 33. The images based on the image data are displayed on the monitor of the liquid crystal display 25. When the acquisition of the image data on the conforming granule sample ends, then an operation similar to the operation in the case of the conforming granule sample is performed on a nonconforming granule sample (including a foreign substance sample) prepared by the skilled operator by means of sorting to acquire image data on the nonconforming granule sample (including a foreign substance sample).

Then, the process proceeds to step 102. Based on the images of the samples displayed on the liquid crystal display 25, the operator visually and roughly specifies, on the images, a sample to be considered to be a conforming granule, a sample to be considered to be a nonconforming granule, and a sample to be considered to be a foreign substance again. Then, the process proceeds to step 103. The specified conforming granule sample image is considered to be one area, and the nonconforming granule sample image is also considered to be one area. A large number of such images are plotted in a three-dimensional color space (in the embodiment, a color space with an R axis, a G axis, and a B axis). Thus, an aggregate is sequentially formed in the RGB color space as depicted in FIG. 7.

(Threshold Calculation Step)

Figure 7:
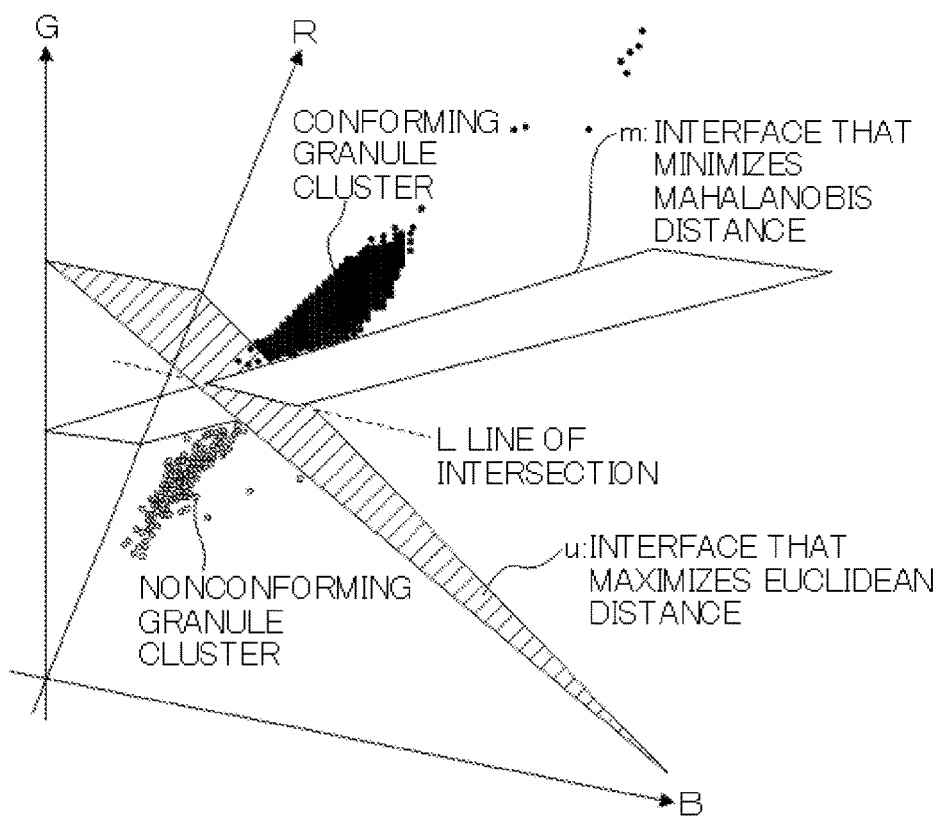
FIG. 7 is an RGB correlation diagram of a conforming granule sample and a nonconforming granule sample on a three-dimensional color space.

In step 104, the data are roughly classified into a cluster (aggregate) formed of dots for conforming granules (black points in FIG. 7) and cluster (aggregate) formed of dots for nonconforming granules (gray points in FIG. 7) (see FIG. 7). In step 105, the statistic of multivariate data is calculated for each of the conforming granule cluster and the nonconforming granule cluster.

The calculation of the statistics may be performed by calculating center-of-gravity vectors or variance/covariance matrices. For example, an arithmetic expression for a center-of-gravity vector is as follows:

[Formula 1]

$$\overline{X} = (\overline{X_1}, \overline{X_2}, \ldots, \overline{X_n}) \quad (1)$$
$$\overline{X_i} = \frac{1}{s}\sigma_{k=1}^{s} X_{ik}$$

S: the number of samples.

Furthermore, an arithmetic expression for a variance/covariance matrix is as follows.

[Formula 2]

$$C_{ij} = \frac{1}{s}\sigma_{K=1}^{s}(X_{ik} - \overline{X_i})(X_{jk} - \overline{X_j}) \quad (2)$$

Then, a Mahalanobis square distance from the center-of-gravity vector for each of the conforming granule/nonconforming granule clusters is determined. Here, the Mahalanobis square distance is a function of the value of multivariate data. An arithmetic expression for the Mahalanobis square distance is as follows.

[Formula 3]

$$D_m^2 = (\alpha - \overline{\alpha_m})^t A^{-1}(\alpha - \overline{\alpha_m}) \quad (3)$$

where m: an index for the cluster,
A: a variance/covariance matrix, and
$\alpha_m$: a center-of-gravity vector for the cluster m.

Then, an interface between the clusters is determined (step 106). When the interface is determined, the values of multivariate data are classified into clusters with the minimum Mahalanobis square distance. For the values of all multivariate data in the multivariate space, the cluster to which the value belongs is determined. Then, the interface depicted by reference character m in FIG. 7 is determined.

Then, a Euclidean distance is selected which involves the longest center-of-gravity distance between a conforming granule cluster and a nonconforming granule cluster, and an interface with a wide effective range of threshold is searched for (step 107). In this regard, when the center-of-gravity vector for the conforming granule cluster is denoted by P(Xp1, Xp2, Xp3, ..., Xpn) and the center-of-gravity vector for the nonconforming granule cluster is denoted by Q(Xq1, Xq2, Xq3, ..., Xqn), the Euclidean square distance between the centers of gravity is expressed by:

[Formula 4]

$$d^2 = \sigma_{l=1}^{n}(X_{p1} - X_{q1})^2 \quad (4)$$

Then, the interface between the clusters is determined (step 107). When the interface is determined, the values of the multivariate data are classified into clusters with the maximum Euclidean square distance, and the interface depicted by reference character u in FIG. 7 is determined.

Then, it is assumed that an equation for the plane m of the interface that minimizes the Mahalanobis distance is expressed by Formula (5), whereas an equation for the plane u of the interface that maximizes the Euclidean distance is expressed by Formula (6).

[Formula 5]

$$m: a_1 x + b_1 y + c_1 z = d_1 \quad (5)$$

$$u: a_2 x + b_2 y + c_2 z = d_1 \quad (6)$$

The two characteristic planes m and u as depicted in FIG. 7 are obtained. Then, the correlation diagram in FIG. 7 is turned such that a viewing direction (viewing vector) aligns with a position where the two different planes m and u intersect each other and appear to be a segment (step 108 in FIG. 5). Thus, the optimum threshold with the number of dimensions in the color space reduced from three to two is determined. This allows provision of an optical type granule sorting machine which allows signal processing to be substantially simplified and which can be easily used by the operator.

A segment L (see FIG. 7) resulting from the intersection of the plane m expressed by Formula (5) and the plane u expressed by Formula (6) can be determined as follows.

[Formula 6]

$$P = A + te \quad (7)$$

where A: a point passing through a line of intersection L,
e: a directional vector for the line of intersection, and
t: a parameter.

Then, when the direction vector e for the line of intersection is determined by executing an exterior substance calculation on normal vectors for the two planes m and u, Formula (7) holds true.

[Formula 7]

$$e = [b1c2 - c1b2 c1a2 - a1c2 a1b2 - b1a2] \quad (8)$$

Here, the following are assumed: Xe=b1c2−c1b2, Ye=c1a2−a1c2, and Ze=a1b2−b1a2.

The point P through which the line of intersection L passes is expressed as follows.

[Formula 8]

For $Ze\neq 0, ((d1b2-d2b1)/Ze, (d1a2-d2a1)/(-Ze), 0)$,

For $Ye\neq 0, ((d1c2-d2c1)/(-Ye), 0, (d1a2-d2a1)/Ye)$,

For $Xe\neq 0, (0, ((d1c2-d2c1)/Xe, (d1b2-d2b1)/(-Xe))$, and

For Xe=0, Ye=0, and Ze=0, no line of intersection is formed (the two planes are parallel to each other)     (9)

Figure 8:
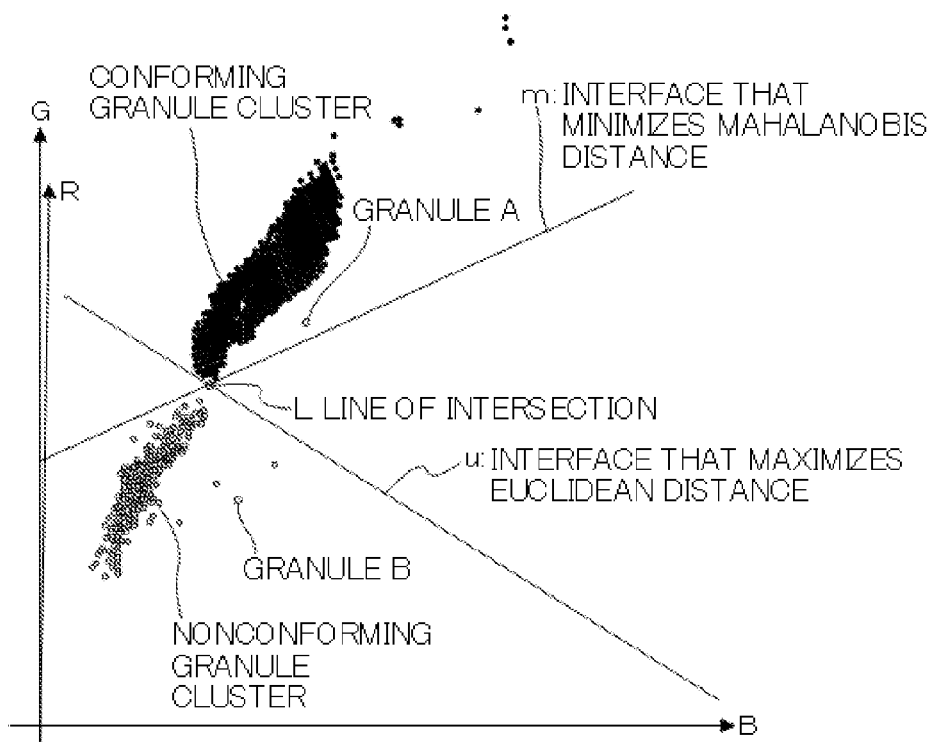
FIG. 8 is an RGB correlation diagram of a conforming granule sample and a nonconforming granule sample on an optimum two-dimensional display surface.

When the line of intersection L is determined as described above, a conversion into an RGB correlation diagram for an optimum two-dimensional display surface with a viewpoint placed on the line of intersection L is enabled (see FIG. 8).

(Threshold Calculation Step)

Then, a determination threshold for conforming granules and nonconforming granules is automatically calculated based on the line of intersection L in the two-dimensional space in FIG. 8 (step 109 in FIG. 5). Step 109 is an important part of the present invention. The threshold calculation step will be described in detail with reference to FIG. 6.

(Details of Threshold Calculation Step)

Figure 6:
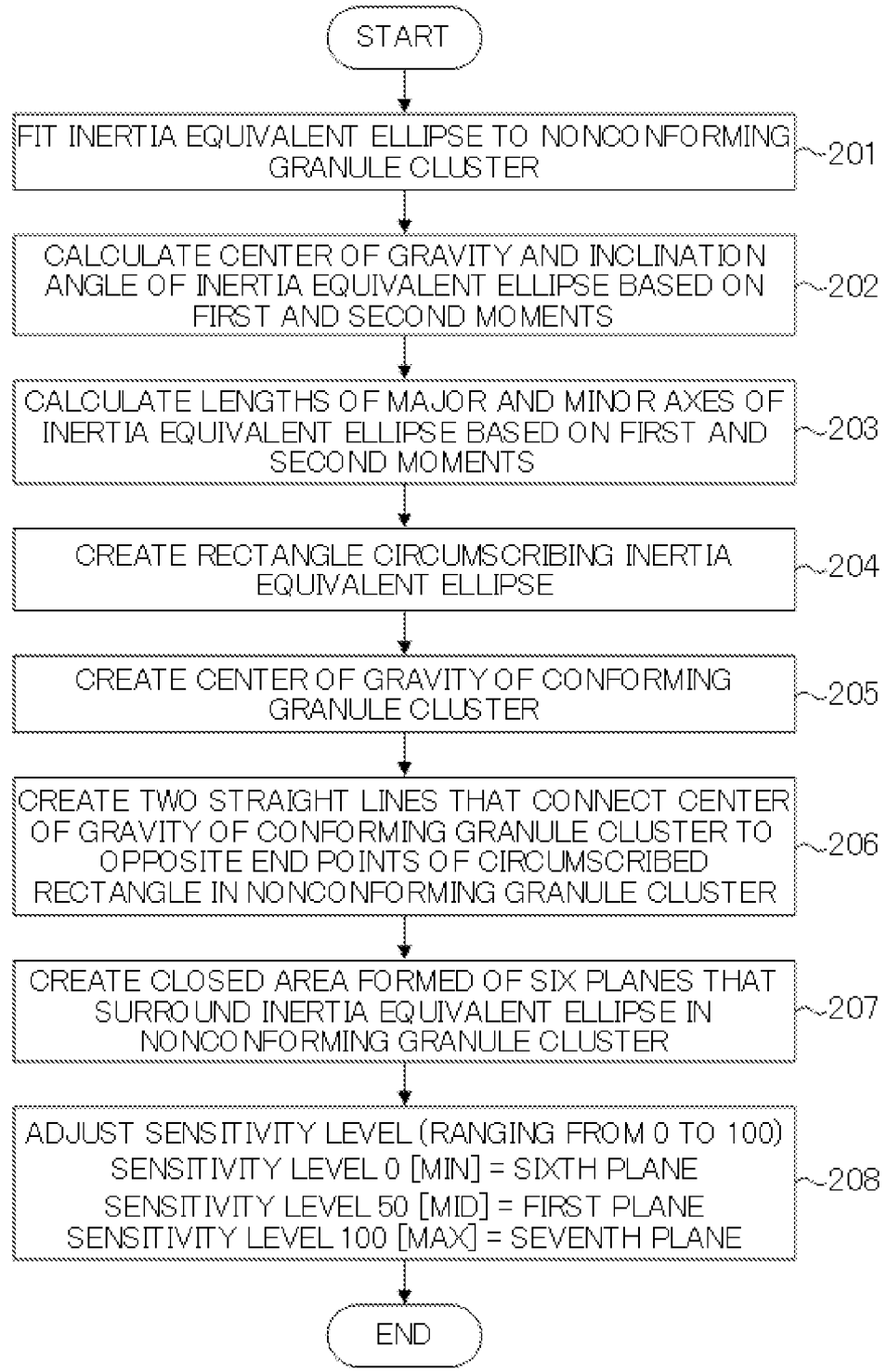
FIG. 6 is a flow diagram depicting a threshold calculation step in detail.

FIG. 6 is a flowchart depicting the threshold calculation step or step 109 in FIG. 5 in detail. The flowchart in FIG. 6 will be described below.

Figure 9:
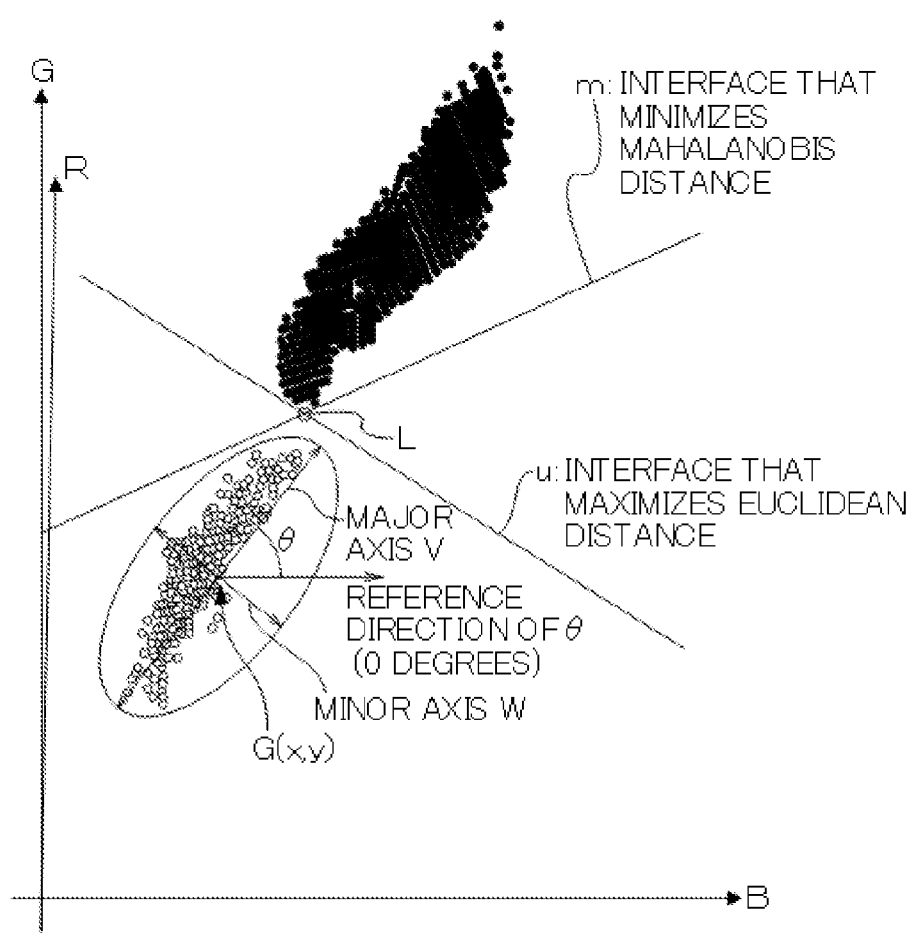
FIG. 9 depicts that an inertia equivalent ellipse is fit to a nonconforming granule cluster on an optimum two-dimensional display surface.

First in step 201, an inertia equivalent ellipse is fit to the nonconforming granule cluster indicated by grey dots in FIG. 8 (see FIG. 9). The inertia equivalent ellipse is a characteristic quantity expressed by an ellipse equivalent to the second moment around the center of gravity roughly equal to the nonconforming granule cluster and allows understanding of the characteristic of the way the nonconforming granule cluster spreads. In practice, to make a nonconforming granule area to be sufficiently larger than the distribution of the nonconforming granule cluster, an inertia equivalent ellipse is so created that the length of the major axis is a multiple of a standard deviation (positive integer multiple) and the length of the minor axis is a multiple of the standard deviation (positive integer multiple). The length of the major axis and the length of the minor axis are empirically set as described above but are preferably changeable freely because the lengths changes as the type of the material changes. In step 202, the center of gravity G and an inclination angle $\theta$ of the direction of the major axis V of the inertia equivalent ellipse are determined. Then, in step 203, the length of the major axis V and the length of the minor axis W are calculated.

Figure 10:
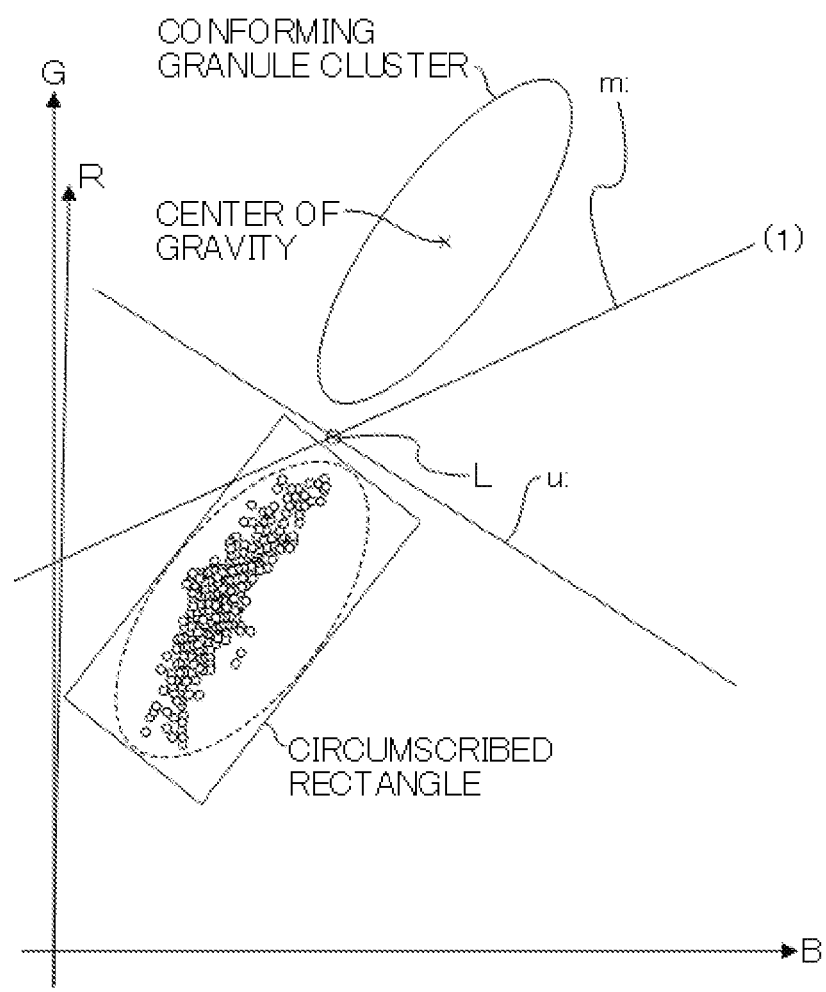
FIG. 10 depicts that a circumscribed rectangle is fit to the inertia equivalent ellipse.

In step 204, two straight lines parallel to the minor axis and passing through opposite end points of the major axis and two straight lines parallel to the major axis and passing through opposite end points of the minor axis are drawn on the inertia equivalent ellipse. That is, the four straight lines create a rectangle that circumscribes the inertia equivalent ellipse (see FIG. 10). The circumscribed rectangle serves as a temporary reference in the automatic sensitivity creation.

Then, in step 205, the center of gravity of the conforming granule cluster is calculated. The calculation is performed by calculating an arithmetic average of all conforming granule data (see FIG. 10).

Figure 11:
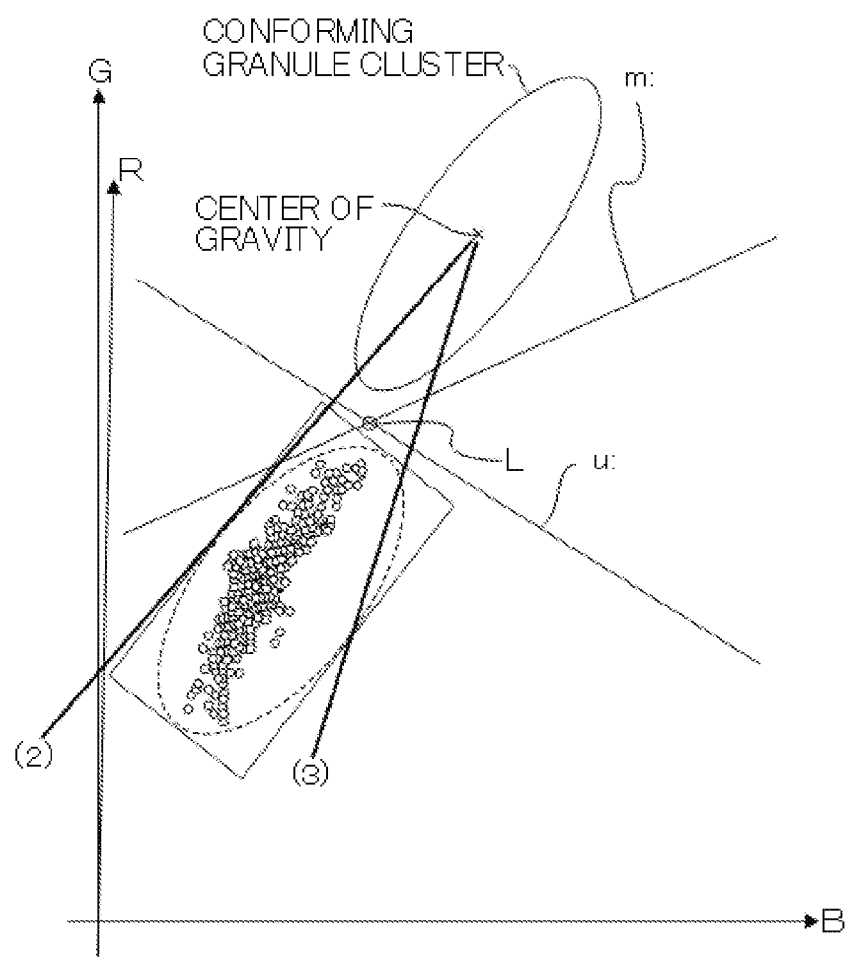
FIG. 11 depicts that two straight lines that connect major-axis opposite end points of the circumscribed rectangle circumscribing the inertia equivalent ellipse to the center of gravity of a conforming granule cluster are created.

To determine the relationship between the conforming granule cluster and the nonconforming granule cluster, the following process is carried out: That is, in step 206, the center of gravity of the conforming granule cluster determined in step 205 is connected to opposite end points of the circumscribed rectangle in the major axis direction in the nonconforming granule cluster determined in step 204 to create two straight lines (see FIG. 11, straight lines labeled with reference numerals (2) and (3)).

Figure 12:
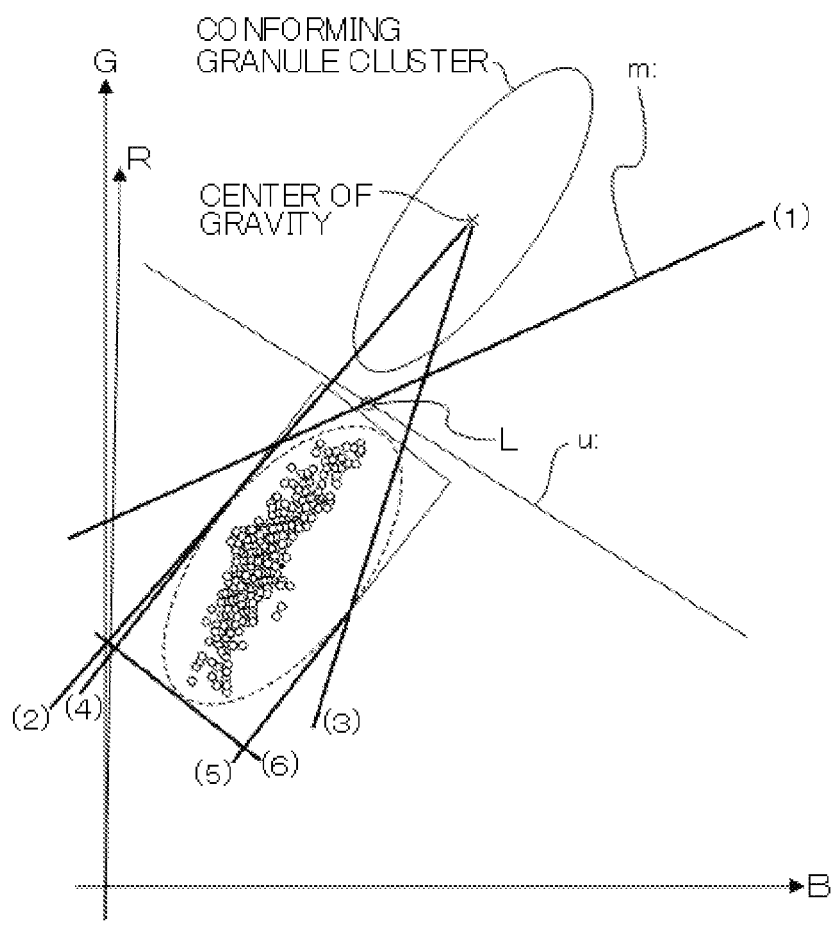
FIG. 12 depicts that six planes are created to form a closed area that surrounds the inertia equivalent ellipse.

The processes described above allow creation of six planes that form a closed area that surrounds the inertia equivalent ellipse fit to the nonconforming granule cluster. That is, as shown in FIG. 12, a first plane is an interface (1) that minimizes the Mahalanobis distance. A second plane is a plane (2) that connects the center of gravity of the conforming granule cluster to one end of the circumscribed rectangle in the major axis direction in the nonconforming granule cluster. A third plane is a plane (3) that connects the center of gravity of the conforming granule cluster to the other end of the circumscribed rectangle in the major axis direction in the nonconforming granule cluster. A fourth plane is a long side (4) on one side of the circumscribed rectangle. A fifth plane is a long side (5) on the other side of the circumscribed rectangle. A sixth plane is a short side (6) of the circumscribed rectangle on one side or on the far side from the conforming granule cluster (see FIG. 12, straight lines labeled with reference numerals (1) to (6)).

The six planes (reference numerals (1) to (6)) that form the closed area described above are determined by drawing a figure, for example, by creating a circumscribed rectangle. The closed area is not necessarily created by drawing a figure and may be stored in a memory in advance in the form of a lookup table (LUT). The complicated calculation process of creating a closed area by drawing a figure can be replaced with a process of referring to a simple matrix for improvement in efficiency.

Figure 13:
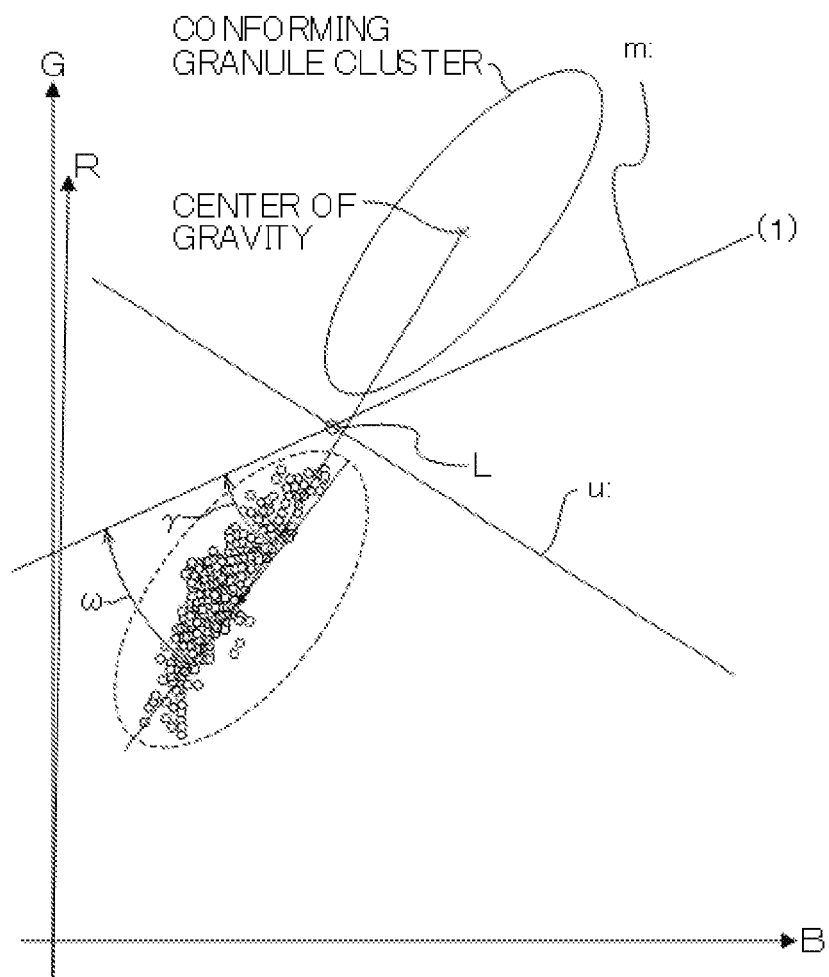
FIG. 13 describes an exception of drawing planes.

As an exception of drawing the planes in the preceding paragraph, when an angle $\gamma$ between the straight line between the centers of gravity of the clusters and the interface (1) (see FIG. 13) and an angle w between the major axis and the interface (1) (see FIG. 13) are both greater than 45°, the fourth and fifth planes described above form the short sides, and the sixth plane described above forms a long side.

The process then proceeds to step 208 in FIG. 6, where the sensitivity is adjusted. The sensitivity level is expressed by a numerical level ranging from 0 to 100. That is, the sensitivity level of 0 is minimum sensitivity (MIN), which does not allow determination of whether a granule in question is a conforming granule or a nonconforming granule, and nonconforming granules may be mixed with conforming granules in the sorting operation, which means poor sensitivity. The sensitivity level of 50 is intermediate sensitivity (MID), which allows precise determination of whether a granule in question is a conforming granule or a nonconforming granule. The sensitivity level of 100 is maximum sensitivity (MAX), which allows highly precise determination of whether a granule in question is a conforming granule or a nonconforming granule but sorts out conforming granules as well as nonconforming granules, which means poor yield.

Figure 14:
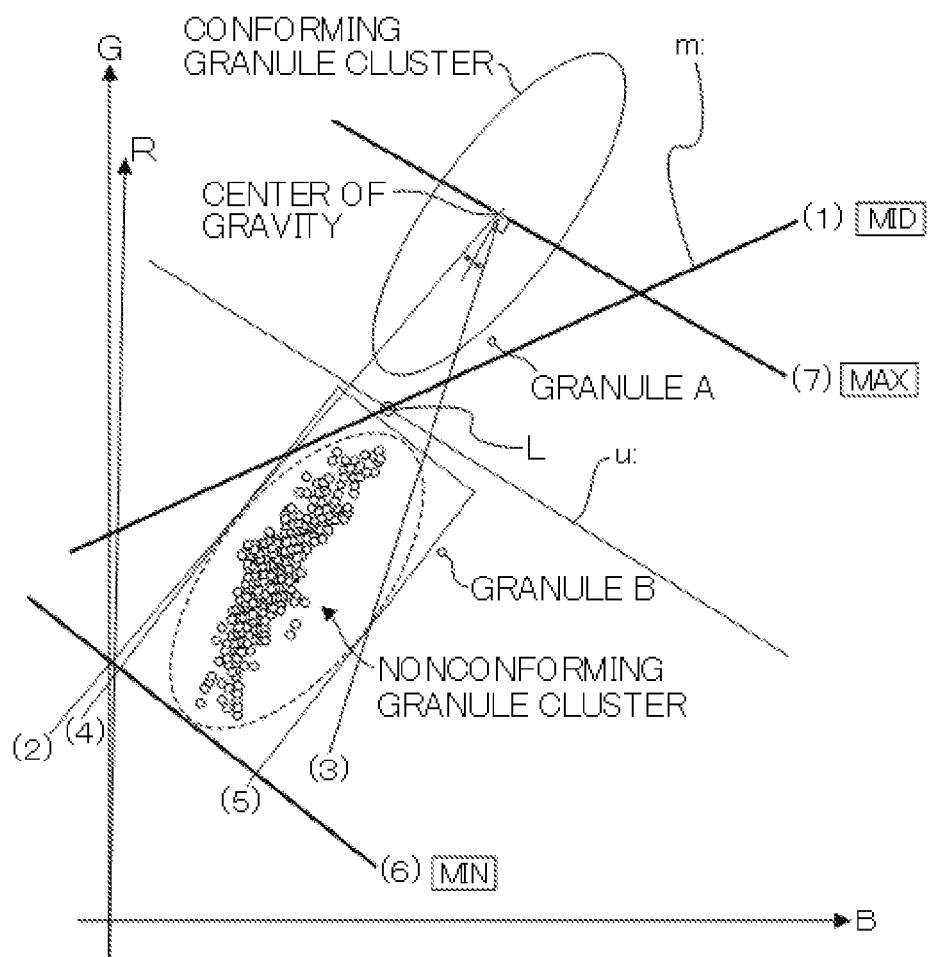
FIG. 14 depicts that calculation of thresholds created by using the six planes that surround the inertia equivalent ellipse is related to three sensitivity levels, minimum, intermediate, and maximum sensitivity levels.

As shown in FIG. 14, the correspondence that relates the calculation of the thresholds created by the six planes that surround an inertia equivalent ellipse described above to the three sensitivity levels, the minimum sensitivity (MIN), the intermediate sensitivity (MID), and the maximum sensitivity (MAX) described above is as follows:

The minimum sensitivity (MIN) corresponds to the sixth plane (6);

the intermediate sensitivity (MID) corresponds to the first plane (1); and the maximum sensitivity (MAX) corresponds to a seventh plane (7) formed by a straight line perpendicular to the straight line that halves the angle between the second plane (2) and the third plane (3).

The three thresholds created by the first plane, the sixth plane, and the seventh plane described above are automatically related to the three sensitivity levels formed of the minimum sensitivity (MIN), the intermediate sensitivity (MID), and the maximum sensitivity (MAX) by pressing a sensitivity creation button 25a disposed on the liquid crystal display 25. Further, since the magnitude of the dimension is lowered from the three-dimensional color space in FIG. 7 to the two-dimensional color space in FIG. 8 for calculation of the threshold, the signal processing can be greatly simplified.

(Sorting Operation)

After the above-described threshold setting operation, the following are performed: specification of a material (grain or granule, the type of the grain, and the like), adjustment of flow rate (setting of a target flow rate), and the like. Subsequently, a material is supplied to the storage tank 5, and a sorting switch on the control panel including a touch panel is selected. Thus, a program that starts a sorting operation is initiated, and the threshold is loaded from the threshold storage memory 34 in FIG. 4, the threshold being set as described above to allow determination of whether the granules are conforming or nonconforming. Then, the signal processing section 31 determines whether the granules are conforming or nonconforming based on the threshold.

In this state, when the vibrating feeder 6 is started, the material supplied to the storage tank 5 is fed onto the chute 4. The material falls from the lower end of the chute 4 and is detected by the optical detectors 7a and 7b.

The current threshold stored in the threshold data storage memory 34 can be schematically depicted as follows: The sensitivity levels described above are so set that they correspond to the sixth plane (6), the first plane (1), and the seventh plane (7) in FIG. 14. For example, as for the first plane (1) in FIG. 14, an area above the plane (1) depicts a conforming granule area, whereas an area below the plane (1) depicts a nonconforming granule area.

In FIG. 14, if a granule A is within the conforming granule area, the conforming granule/nonconforming granule determination mechanism 36 in FIG. 4 determines that the "granule A is a conforming granule." In this case, the ejector driving circuit 41 issues no removal signal, and the granule A is collected in the conforming granule faucet 28 (see FIG. 2) as a conforming granule. If a granule B is within the nonconforming granule area, the conforming granule/nonconforming granule determination mechanism 36 in FIG. 4 determines that the "granule B is a nonconforming granule." In this case, the ejector driving circuit 41 issues a removal signal to the solenoid valve 21. The granule B is removed from the material flowing downward by high-pressure air blown through the ejector nozzle 8. The granule B is then collected in the nonconforming granule faucet 27 (see FIG. 2).

The opposite setting may be made by considering the conforming granule cluster in FIG. 7 and FIG. 8 to be a nonconforming granule cluster, while considering the nonconforming granule cluster in FIG. 6 and FIG. 7 to be a conforming granule cluster. Normally, the nonconforming granules account for a very low percentage of the material compared to the conforming granules and can thus be sorted and removed by blowing high-pressure air from the ejector nozzle 8 against the nonconforming granules. However, if the conforming granules accounts for a very low percentage of the material compared to the nonconforming granules, sorting efficiency is increased by considering the conforming granules to be nonconforming granules and blowing high-pressure air from the ejector nozzle 8 against the conforming granules to sort and remove the conforming granules. This is referred to as "reverse out", and a relevant control mechanism is conventionally incorporated into a color sorting machine. The operator can set as appropriate whether the normal setting is used or the reverse-out is used, taking into account, for example, the rate of nonconforming granules mixed in the material granules. Simply rewriting the data in the threshold data storage memory 34 readily allows setting of an operation of considering the conforming granule cluster in FIG. 7 and FIG. 8 to be a nonconforming granule cluster, while considering the nonconforming granule cluster in FIG. 7 and FIG. 8 to be a conforming granule cluster. When the operator sets "reverse out", the conforming granules are subjected to high-pressure air from the ejector nozzle 8 and collected in the nonconforming granule faucet 27. On the other hand, the nonconforming granules are collected in the conforming granule faucet 28 without being subjected to high-pressure air from the ejector nozzle 8.

As described above, the present invention relates to an optical type granule sorting machine comprising transfer means for transferring granules including conforming granules, nonconforming granules, and foreign substances in such a manner that the granules form a continuous flow, inspection means for inspecting the granules transferred by the transfer means, determination means for determining whether or not the granules are to be treated as a separation target based on information on color of the individual granules inspected by the inspection means, and exclusion means for excluding the separation target determined by the determination means from the continuous flow. The inspection means includes an illumination section that illuminates the granules with light and an optical detection section that detects light transmitted through the granules or reflected from the granules. The determination means includes a three-dimensional color distribution data creation section that plots wavelength components of R light, G light, and B light from the granules detected by the optical detection section in a three-dimensional color space to create three-dimensional color distribution data for a granule sample, a Mahalanobis distance interface creation section that sets an interface calculated based on a Mahalanobis distance in the three-dimensional color distribution data created by the three-dimensional color distribution data creation section to partition the data into a first conforming granule cluster area containing many conforming granules and a first nonconforming granule cluster area containing many nonconforming granules and foreign substances, a Euclidean distance interface creation section that determines a position of center of gravity of the first conforming granule cluster area created by the Mahalanobis distance interface creation section and a position of center of gravity of the first nonconforming granule cluster area created by the Mahalanobis distance interface creation section, the Euclidean distance interface creation section setting an interface calculated based on a Euclidean distance at which the positions of center of gravity lie at a longest distance from each other to partition the data into a second conforming granule cluster area and a second nonconforming granule cluster area, a two-dimensional data conversion section that determines a line of intersection between the interface calculated based on the Mahalanobis distance and the interface calculated based on the Euclidean distance and converts the three-dimensional color distribution data into two-dimensional color distribution data in such a way that a viewpoint is placed on the line of intersection, and a threshold setting section that creates a closed area by fitting an inertia equivalent ellipse to the nonconforming granule cluster area on the two-dimensional color distribution data converted by the two-dimensional data conversion section and sets a threshold in the closed area. Thus, the granule sample plotted in the three-dimensional color space is generally separated into the conforming granule cluster area and the nonconforming granule cluster area based on the Mahalanobis distance interface. Then, an interface with a wide effective range of sensitivity is searched for based on the Euclidean distance interface. Moreover, the threshold setting section can calculate a threshold in a two-dimensional color space. Thus, an operator can easily perform sensitivity setting by effectively utilizing RGB three-dimensional color space information similar to information acquired via human eyes, and signal processing can also be substantially simplified. In the sensitivity adjustment, since a closed area is created by fitting an inertia equivalent ellipse to the nonconforming granule cluster and a threshold is set in the area, the threshold is automatically set with no operator's decision, knowhow, or other abilities, whereby the machine is readily operated and the convenience of the machine is greatly enhanced.

The color sorting machine according to the present invention is not limited to the above-described embodiment. Various changes may be made to the design of the embodiment. For example, the chute is adopted as the transfer means, but may be configured to include a plurality of stages such as two vertical stages or three vertical stages. Alternatively, a belt conveyor or the like may be used instead of the chute. Furthermore, the high-speed air ejector nozzle that blows high-pressure air is adopted as the exclusion means for excluding the separation target from the continuous flow. However, instead of the high-speed ejector nozzle, a push ejector means such as an air cylinder may be used which excludes the separation target from the continuous flow.

As described above, the present invention is evidently a novel and useful optical type granule sorting machine which allows sensitivity setting to be easily performed by effectively utilizing RGB three-dimensional color space information similar to information obtained via human eyes and which enables signal processing to be substantially simplified.

INDUSTRIAL APPLICABILITY

The present invention is applicable to an optical type granule sorting machine that sorts a material including grains such as rice, wheat, beans, or nuts, resin pieces such as pellets or beads, medicines, ores, fine articles such as white baits, or other granules into conforming granules and nonconforming granules and excludes foreign substances or the like mixed in the material.

REFERENCE SIGNS LIST

1 Optical type granule sorting machine
2 Machine frame
3A Primary sorting section
3B Secondary sorting section
4 Chute
5 Storage tank
6 Vibrating feeder
7 Optical detection section
8 Ejector nozzle
9 Conforming granule collection gutter
10 Nonconforming granule collection gutter
11 Auxiliary nonconforming granule collection gutter
12 Box
13 CCD camera
14 NIR camera
15 Visible light source
16 Near infrared light source
17 Background
18 Window member
19 Subtank
20 Air pipe
21 Solenoid valve
22 Tube
23 Air cylinder
24 Front door
25 Liquid crystal display
26 Power supply switch
27 Nonconforming granule faucet
28 Conforming granule faucet
29 Auxiliary nonconforming granule faucet
30 Sample slot
31 Signal processing section
32 CPU and memory section
33 Image data acquisition mechanism
34 Threshold data storage memory
35 Binarization calculation mechanism
36 Conforming granule/nonconforming granule determination mechanism
37 Image data storage memory
38 Threshold data calculation mechanism
39 Operation signal reception mechanism
40 Ejector driving circuit

What is claimed is:

1. An optical type granule sorting machine comprising:
transfer means for transferring granules including conforming granules, nonconforming granules, and foreign substances in such a manner that the granules form a continuous flow;
inspection means for inspecting the granules transferred by the transfer means;
determination means for determining whether or not the granules are to be treated as a separation target based on information on color of the individual granules inspected by the inspection means; and
exclusion means for excluding the separation target determined by the determination means from the continuous flow,
wherein the inspection means includes an illumination section that illuminates the granules with light and an optical detection section that detects light transmitted through the granules or reflected from the granules, and
the determination means includes
a three-dimensional color distribution data creation section that plots wavelength components of R light, G light, and B light from the granules detected by the optical detection section in a three-dimensional color space to create three-dimensional color distribution data for a granule sample,
a Mahalanobis distance interface creation section that sets an interface calculated based on a Mahalanobis distance in the three-dimensional color distribution data created by the three-dimensional color distribution data creation section to partition the data into a first conforming granule cluster area containing many conforming granules and a first nonconforming granule cluster area containing many nonconforming granules and foreign substances, a Euclidean distance interface creation section that determines a position of center of gravity of the first conforming granule cluster area created by the Mahalanobis distance interface creation section and a position of center of gravity of the first nonconforming granule cluster area created by the Mahalanobis distance interface creation section, the Euclidean distance interface creation section setting an interface calculated based on a Euclidean distance at which the positions of centers of gravity lie at a longest distance from each other to partition the data into a second conforming granule cluster area and a second nonconforming granule cluster area, a two-dimensional data conversion section that determines a line of intersection between the interface calculated based on the Mahalanobis distance and the interface calculated based on the Euclidean distance, converts the three-dimensional color distribution data into two-dimensional color distribution data in such a way that a viewpoint is placed on the line of intersection to separate the granule sample into a conforming granule cluster area and a nonconforming granule cluster based on the line of intersection, and a threshold setting section that adjusts sensitivity of the determination means by creating a closed area by fitting an inertia equivalent ellipse to the nonconforming granule cluster area on the two-dimensional color distribution data converted by the two-dimensional data conversion section and setting a threshold in the closed area to allow determination of whether or not the nonconforming granule cluster is to be treated as a separation target by the determination means.

2. The optical type granule sorting machine according to claim 1, wherein the threshold setting section that creates a closed area by fitting an inertia equivalent ellipse to the nonconforming granule cluster area on the two-dimensional color distribution data and sets a threshold in the closed area includes means for creating a circumscribed rectangle formed of two straight lines parallel to a minor axis of the inertia equivalent ellipse and passing through opposite end points of a major axis of the inertia equivalent ellipse and two straight lines parallel to the major axis and passing through opposite end points of the minor axis and means for creating two straight lines that connect the center of gravity of the conforming granule cluster to opposite end points of the circumscribed rectangle in the major axis direction.

3. The optical type granule sorting machine according to claim 2, wherein the threshold setting section that creates a closed area by fitting an inertia equivalent ellipse to the nonconforming granule cluster area on the two-dimensional color distribution data and sets a threshold in the closed area uses an interface that minimizes the Mahalanobis distance as a first plane, uses a plane that connects the center of gravity of the conforming granule cluster to one end of the circumscribed rectangle in the major axis direction as a second plane, uses a plane that connects the center of gravity of the conforming granule cluster to another end of the circumscribed rectangle in the major axis direction as a third plane, uses a long side of the circumscribed rectangle on one side as a fourth plane, uses a long side of the circumscribed rectangle on another side as a fifth plane, and uses a short side of the circumscribed rectangle on one side or on a far side from the conforming granule cluster as a sixth plane.

* * * * *